United States Patent [19]

Parker et al.

[11] Patent Number: 4,902,625

[45] Date of Patent: Feb. 20, 1990

[54] RAPID CORROSION TEST FOR ZIRCONIUM AND ZIRCONIUM ALLOY WELDMENTS

[75] Inventors: Donald W. Parker; Merle A. Parker, both of Columbia, S.C.; George P. Sabol; Isabel K. Lloyd, both of Murrysville Boro, Pa.

[73] Assignee: Westinghouse Electric Corp., Pittsburgh, Pa.

[21] Appl. No.: 353,188

[22] Filed: May 16, 1989

Related U.S. Application Data

[63] Continuation of Ser. No. 680,423, Dec. 11, 1984, abandoned.

[51] Int. Cl.$^4$ ............................................. G01N 17/00
[52] U.S. Cl. ................................. 436/6; 148/128; 148/242; 356/36; 422/53; 436/83; 436/908
[58] Field of Search ............... 436/6, 83, 908; 73/61.2, 86; 422/7, 53; 148/6.11, 128, 421; 420/422; 75/235; 376/305; 106/14.05, 28.4; 356/36

[56] References Cited

U.S. PATENT DOCUMENTS

| | | | |
|---|---|---|---|
| 2,987,352 | 6/1961 | Watson | 308/241 |
| 4,212,686 | 7/1980 | Lunde et al. | 420/422 |
| 4,440,862 | 4/1984 | Cheng et al. | 436/6 |

FOREIGN PATENT DOCUMENTS

| | | | |
|---|---|---|---|
| 0020644 | 2/1982 | Japan | 436/6 |
| 0587371 | 1/1978 | U.S.S.R. | 436/6 |
| 2132345 | 7/1984 | United Kingdom . | |

OTHER PUBLICATIONS

Cox, Oxidation of Metals, vol. 3, No. 5, pp. 399–430, 1971.
American Society for Testing and Materials (ASTM), Test Designation G2-81, 1981.
Henthorne, Corrosion Nace, vol. 30, No. 2, pp. 39–46, 1974.
Manning et al., Metal Progress, No. 2, pp. 31–37, 1982.
Cox, Chemical Abstracts, vol. 76, Abstract No. 17248d, 1972.
Ramasubramanian, J. Electrochem. Soc. vol. 127, No. 12, pp. 2566–2572, 1980.
Ramasubramanian, J. Electrochem. Soc., vol. 128, No. 1, pp. 68–75, 1981.

*Primary Examiner*—Robert J. Hill, Jr.
*Attorney, Agent, or Firm*—A. Mich, Jr.

[57] ABSTRACT

The present invention is a method of rapidly and reproducibly checking the quality of zirconium base material welds and heat affected zones. In this method, weldment samples are immersed in an elevated temperature fused salt bath for a time period sufficient, at the bath temperature selected, to produce an essentially black oxide film in acceptable quality welds while producing a scaling oxide in unacceptable welds.

16 Claims, 1 Drawing Sheet

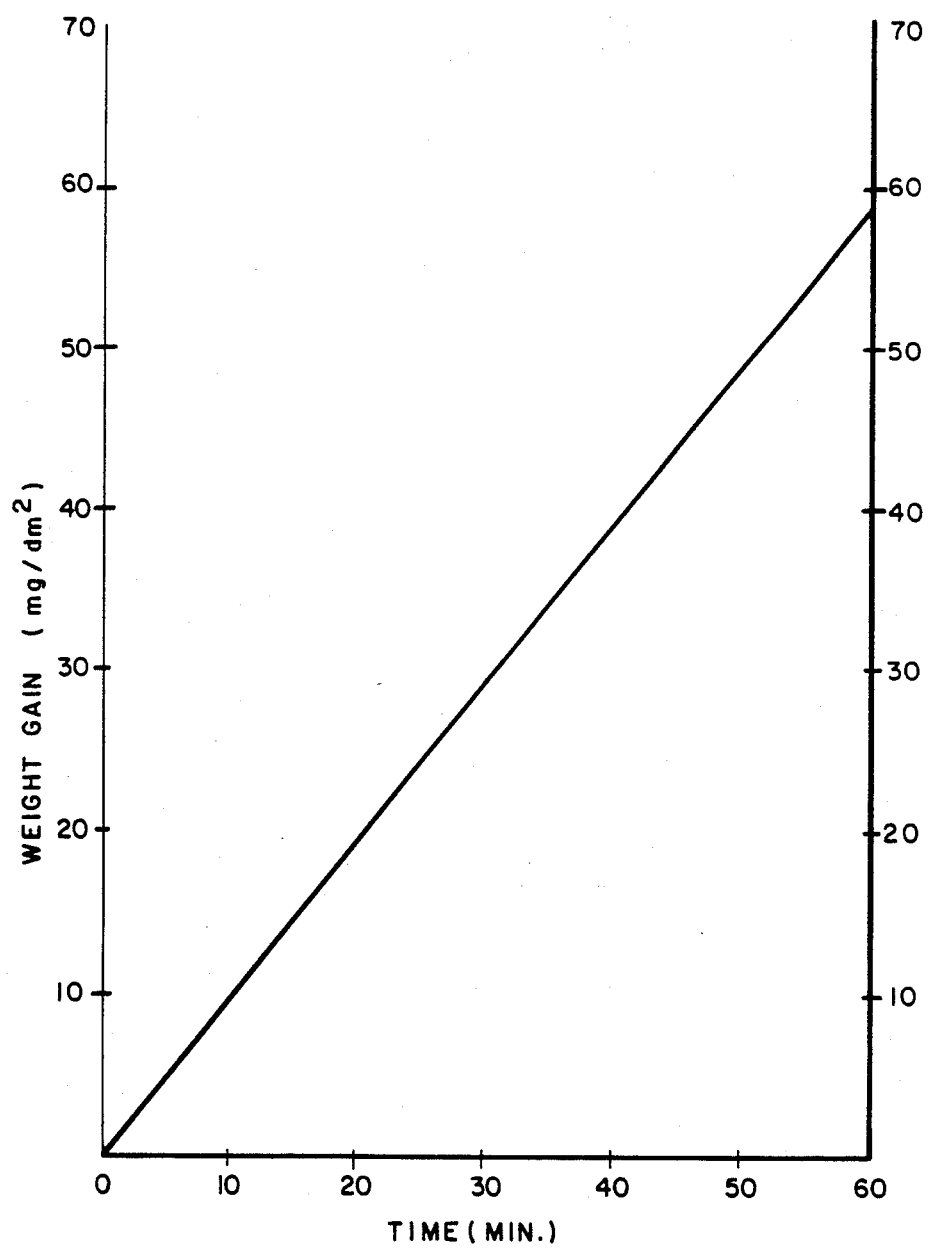

RAPID CORROSION TEST FOR ZIRCONIUM AND ZIRCONIUM ALLOY WELDMENTS

This application is a continuation of application Ser. No. 680,423 filed Dec. 11, 1984, and now abandoned.

BACKGROUND OF THE INVENTION

The present invention relates to the field of corrosion testing of zirconium and zirconium base alloys and is most particularly concerned with the corrosion testing of zirconium alloy weldments.

Zirconium alloys are commonly used in commercial pressurized water and boiling water nuclear reactors for structural elements such as fuel rod channels and grids, and as heat transfer elements such as tubular fuel cladding. One of the most common methods of joining one zirconium alloy member to another to form the aforementioned elements is by welding.

Zirconium and its alloys are well known to be highly reactive materials at high temperatures; that is, they readily, and rapidly, combine with oxygen and nitrogen in the atmosphere. It is known that the contamination of zirconium alloys with these elements can adversely affect the aqueous corrosion resistance and/or mechanical properties of the alloy. It is therefore common practice in the welding of zirconium alloy nuclear components to perform all welding in an inert atmosphere such as in a vacuum, or in a helium or argon atmosphere. For example, the girth welds joining Zircaloy-4 end plugs to the ends of Zircaloy-4 fuel cladding are typically formed by Tungsten Inert Gas (TIG) welding in a helium-filled chamber. To assure that air is not leaking into the welding chamber and contaminating the weldment, weldment samples are periodically subjected to a three-day 360° C. (680° F.) water corrosion test (ASTM Test No. G2).

While this test is very successful in detecting weldment samples having harmful impurity levels, especially nitrogen, it is time consuming. It takes three, to as long as seven days, to obtain test results. Due to this long turnaround time, the three-day water test is of little value as a process control test. Also, the storage space required for welded product awaiting acceptable test results is costly and increases inventory control problems. It is therefore desirable to develop a test which is as capable as the three-day water test in detecting weldments with deleterious impurity levels, but which is significantly more rapid.

BRIEF SUMMARY OF THE INVENTION

We have discovered a rapid corrosion test which fulfills the aforementioned need, in that our test takes less than one hour, while maintaining an accuracy commensurate with the commercial 360° C. water test method now in use. Our test involves taking a zirconium or zirconium alloy weldment, which includes the weld and heat affected zones (HAZ), and immersing it into an elevated temperature fused salt bath, preferably maintained at a temperature above about 400° C.

The temperature of the fused salt bath and the duration of the immersion are controlled to produce an essentially black, adherent oxide film in corrosion resistant weldments, while producing a white scaling oxide corrosion product in contaminated, noncorrosion resistant weldments. After removal from the fused salt bath, the weldment sample is evaluated for scaling oxide corrosion product.

Preferably, the fused salt bath is composed of a mixture of $NaNO_3$, $KNO_3$, and $KI$.

Preferably, the salt bath temperature and test duration are controlled to produce an adherent oxide weight gain in corrosion resistant Zircaloy-4 of between about 6 to about 16 $mg/dm^2$.

Preferably, the temperature of the bath is maintained between about 400° C. (750° F.) and about 500° C. (932° F.) with a bath temperature of about 460° C. (860° F.) to about 482° C. (900° F.) being more preferred. The duration of immersion is preferably between about 2.5 to about 16 minutes with a duration of about 5 to about 10 minutes being most preferred.

These and other aspects of the present invention will become more apparent upon review of the figure in conjunction with the detailed description of the invention.

BRIEF DESCRIPTION OF THE DRAWING

The FIGURE shows the correlation between the oxide film weight gain of Zircaloy-4 test coupons and the duration of immersion in the fused salt bath.

DETAILED DESCRIPTION OF THE INVENTION

In accordance with the present invention, we have found that our best results have been achieved when using a fused salt bath composed of:

about 48.6 weight % $NaNO_3$
about 41.0 weight % $KNO_3$
about 10.4 weight % $KI$ held at a temperature of about 460° C. (860° F.) to 482° C. (900° F.) with a Zircaloy-4 weldment immersion time of about 2.5 to about 16 minutes, and more preferably, about 5 to about 10 minutes. It is, however, our belief that the above parameters can be varied in accordance with the following guidelines while still achieving excellent results.

The controlling of the combination of time of immersion and temperature is believed to be critical. The time of immersion and the temperature of the bath should be controlled to produce an essentially black, adherent oxide film in corrosion resistant weldments while producing a white scaling oxide corrosion product in contaminated, noncorrosion resistant weldments. The range of values of this time-temperature combination will vary in accordance with the particular salt bath used, and the oxidation kinetics of the particular metal or alloy (e.g., zirconium, Zircaloy-2, Zircaloy-4, zirconium 2.5 weight % niobium). For example, in Zircaloy-4 it is known that the conventional three-day water test produces an oxide weight gain in high quality Zircaloy-4 weldment samples of about 6 to 16 milligrams/square decimeter ($mg/dm^2$). It was therefore one of our goals when testing Zircaloy-4 weldments in accordance with our invention to select time-temperature combinations which will also produce weight gains between about 6–16 $mg/dm^2$ in noncontaminated Zircaloy-4 weldments.

The FIGURE shows that for immersion in a 48.6 weight % $NaNO_3$–41.0 weight % $KNO_3$–10.4 weight % $KI$ fused salt bath held at 460° to 482° C., the time necessary to produce the aforementioned weight gain is about 6 to 16 minutes. However, our tests have shown that immersion times as short as 2.5 minutes can still distinguish contaminated Zircaloy-4 weldments. While immersion times as short as 0.5 minute may still distinguish unacceptable from acceptable product, we prefer, in order to optimize the reproducibility of the test results, that the immersion time be held to about 2.5 to 16 minutes, and more preferably, to about 5 to about 10 minutes. At times longer than about 10 minutes spurious oxide scaling, unrelated to contamination, may occur with increasing frequency and interfere with the accurate evaluation of the test results.

Salt bath temperatures as low as 400° C. and as high as about 500° C. are also contemplated. The immersion time, however, is required to reproducibly distinguish contaminated material expected to vary with the bath temperature. For example, for bath temperatures around 400° C., the immersion time to produce a weight gain of 6 to 16 mg/dm$^2$ will be significantly longer than the about 5 to 16 minutes required to 460° to 482° C., while the immersion time to produce the same weight gain at about 500° C. will be reduced.

While the composition of the salt bath is important to achieving the results described, it is not believed to be critical. It is therefore contemplated that other ratios of $NaNO_3$ to $KNO_3$ to $KI$ may be used, and that other substantially equivalent salt mixtures may also be substituted. While reagent grade $NaNO_3$, $KNO_3$, and $KI$ has been utilized in the following examples, it is believed that commercial grades of these salts will produce similar results.

The foregoing aspects of the present invention will be further clarified by consideration of the following examples which are intended to be purely exemplary of the present invention.

EXAMPLE 1

Seventy-five (75) Zircaloy-4 test coupons were submitted for salt bath corrosion testing on eight different days over a three-week period. The fused salt bath utilized was a mixture of reagent grade salts producing the following mixture:

48.6 weight % $NaNO_3$
41.0 weight % $KNO_3$
10.4 weight % $KI$

The bath temperature was set at 460° C. with an actual range of 460° to 482° C. Prior to immersion, all coupons were cleaned with isopropanol. The duration of immersion used was varied and included the following durations (in minutes):

2.5, 5, 7.5, 10, 12.5, 15, 20, 30, 45, 60.

Upon removal from the salt bath, the coupons were quenched in water and any adhering salt was rinsed off. The oxide weight gain of each coupon was then measured. The results, shown graphically in the FIGURE, indicate a straight line correlation passing through the origin with a slope of about 1. Least squares analysis of the data yield:

weight gain (mg/dm$^2$) = [time (min.) × 0.982] − 0.183

(with $R^2$ = 0.984).

Test coupons submitted for three-day water autoclave tests showed weight gains of 6.1–16.1 mg/dm$^2$. The optimum salt bath test duration to match the weight gains observed in the conventional three-day water test is about 6 to about 16 minutes.

EXAMPLE II

In order to demonstrate the ability of the present invention to accurately predict three-day water corrosion test results, Zircaloy-4 end plugs (having a Zircaloy-4 weldment) were cut from rods that had been rejected due to slight atmosphere contamination as detected in the thee-day water corrosion test. Fifty (50) end plugs were given the three-day water test in five separate autoclave runs. Results from these tests (see Table I) showed a 38% failure rate (i.e., scaling oxide in the weld and/or heat affected zone).

TABLE I

| | Three-Day Autoclave Test | | | |
|---|---|---|---|---|
| | Number Tested | Number Pass | Number Fail | Percent Failure |
| Day 1 | 10 | 7 | 3 | 30 |
| Day 2 | 10 | 5 | 5 | 50 |
| Day 3 | 10 | 8 | 2 | 20 |
| Day 4 | 10 | 5 | 5 | 50 |
| Day 5 | 10 | 6 | 4 | 40 |
| Total | 50 | 31 | 19 | 38 |

Seventy-five (75) end plugs were then tested using the salt bath technique described in Example I. Tests were conducted on eight different days and at six different test durations ranging from 2.5 to 15 minutes. After immersion, the samples were evaluated for the presence of white scaling oxide on the weld and/or heat affected zones of the weldment, as an indication of atmospheric contamination during welding. The overall failure rate was 40% (30/75). (See Tables II and III.)

TABLE II

| | Rapid Corrosion Test | | | |
|---|---|---|---|---|
| Test Duration | Number Tested | Number Pass | Number Fail | Percent Failure |
| 2.5 Min. | 20 | 13 | 7 | 35 |
| 5.0 Min. | 25 | 12 | 13 | 52 |
| 7.5 Min. | 9 | 5 | 4 | 44 |
| 10.0 Min. | 9 | 7 | 2 | 22 |
| 12.5 Min. | 4 | 3 | 1 | 25 |
| 15.0 Min. | 8 | 5 | 3 | 38 |
| Total | 75 | 45 | 30 | 40 |

TABLE III

| | Rapid Corrosion Test | | | |
|---|---|---|---|---|
| Test Day | Number Tested | Number Pass | Number Fail | Percent Failure |
| Day 1 | 5 | 4 | 1 | 20 |
| Day 2 | 10 | 6 | 4 | 40 |
| Day 3 | 10 | 7 | 3 | 30 |
| Day 4 | 10 | 5 | 5 | 50 |
| Day 5 | 10 | 6 | 4 | 40 |
| Day 6 | 10 | 6 | 4 | 40 |
| Day 7 | 10 | 7 | 3 | 30 |
| Day 8 | 10 | 4 | 6 | 60 |
| Total | 75 | 45 | 30 | 40 |

The test duration and test date had no apparent effect on the failure rate of samples submitted to the salt bath. Samples tested for 5–7.5 minutes were the easiest to examine visually. At test durations longer than 7.5 minutes, a spurious scale formation was seen on all plugs. This scale formation was attributed to base metal corrosion and not considered as a failure (i.e., it was not associated with the weld metal or heat affected zones).

EXAMPLE III

To further examine the scale formation, several plugs were tested in the salt bath using the technique used in Examples I and II with one exception. Samples were removed every 30 seconds for visual examination only (no quenching). Failed plugs showed evidence of scale formation as early as 30 sec. into the test.

In the preceding examples, the fused salt bath temperature was controlled between about 460° and about 482° C., a range of about 22° C. It is believed tha the test may be further improved by tighter control of the temperature during immersion. A temperature range of about 6° C. is contemplated (e.g. about 460° to about 466° C.).

While our invention has been described with respect to the detection of atmospheric contamination during welding, it is presently contemplated that those of ordinary skill in the art may also utilize this test to detect tungsten and/or uranium contamination as well, with any modification, which may be necessary, well within their skill after reading the foregoing specification.

Other embodiments of the invention will be apparent to those skilled in the art from a consideration of this specification or practice of the invention disclosed thereon. It is intended that the specification and examples be considered as exemplary only, with the true scope and spirit of the invention being indicated by the following claims.

We claim:

1. A method of determining corrosion resistance of a zircaloy weld and heat affected zones comprising the steps of:
   (a) immersing said zircaloy weld and heat affected zones into a fused salt bath having a temperature above about 400° C.;
   (b) controlling the temperature of said fused salt bath and duration of said immersion to produce an essentially black oxide film in corrosion resistant zircaloy weld and heat affected zones, while producing a white oxide scale in noncorrosion resistant zircaloy welds and heat affected zones;
   (c) removing said zircaloy weld and heat affected zones from said salt bath after said duration; and
   (d) evaluating the oxide produced on said zircaloy weld and heat affected zones for the presence of a white scaling oxide.

2. The method according to claim 1 wherein said temperature of said fused salt bath and said duration of said immersion are controlled to produce an oxide weight gain in corrosion resistant Zircaloy-4 of about 6 to about 16 mg/dm$^2$.

3. The method according to claim 2 wherein said temperature of said fused salt bath is controlled to be between about 460° C. to about 466° C.

4. The method according to claim 2 wherein said duration of said immersion is between about 5 to about 10 minutes.

5. The method according to claim 2 wherein said fused salt bath consists essentially of $NaNO_3$, $KNO_3$, and KI.

6. The method according to claim 2 wherein said fused salt bath consists essentially of about 48.6 weight % $NaNO_3$, about 41 weight % $KNO_3$, and about 10.4 weight % KI.

7. The method according to claim 2 wherein said temperature of said fused salt bath is controlled to be between about 460° C. and about 482° C.

8. The method according to claim 7 wherein said fused salt bath consists essentially of $NaNO_3$, $KNO_3$, and KI.

9. The method according to claim 7 wherein said fused salt bath consists essentially of about 48.6 weight % $NaNO_3$, about 41 weight % $KNO_3$, and about 10.4 weight % KI.

10. The method according to claim 7 wherein said duration of said immersion is between about 5 to about 10 minutes.

11. The method according to claim 10 wherein said fused salt bath consists essentially of $NaNO_3$, $KNO_3$, and KI.

12. The method according to claim 10 wherein said fused salt bath consists essentially of about 48.6 weight % $NaNO_3$, about 41 weight % $KNO_3$, and about 10.4 weight % KI.

13. The method according to claim 1 wherein said temperature of said fused salt bath is controlled to be between about 400° and about 500° C.

14. The method according to claim 1 wherein said duration of said immersion is between about 2.5 and 16 minutes.

15. The method according to claim 1 wherein said fused salt bath consists essentially of $NaNO_3$, $KNO_3$, and KI.

16. The method according to claim 1 wherein said fused salt bath consists essentially of about 48.6 weight % $NaNO_3$, about 41 weight % $KNO_3$, and about 10.4 weight % KI.

* * * * *